US Patent Number: 4,535,485
Ashman et al.
Date of Patent: Aug. 20, 1985

[54] POLYMERIC ACRYLIC PROTHESIS

[75] Inventors: Arthur Ashman, New York, N.Y.; Paul F. Bruins, Austin, Tex.

[73] Assignee: Medical Biological Sciences, Inc., New York, N.Y.

[21] Appl. No.: 357,739

[22] Filed: Mar. 12, 1982

[51] Int. Cl.$^3$ .......................... A61F 1/00; A61F 5/04
[52] U.S. Cl. .................................. 623/16; 128/92 C; 128/92 G; 623/10
[58] Field of Search ................... 427/2; 433/201; 3/1, 3/1.9, 1.911, 1.912, 1.913; 128/92 C, 92 CA, 92 G

[56] References Cited

U.S. PATENT DOCUMENTS

| | | |
|---|---|---|
| Re. 24,401 | 7/1974 | Wicherle et al. |
| 3,628,248 | 12/1971 | Kroder ........................... 433/201 X |
| 3,628,988 | 12/1971 | Stol et al. |
| 3,632,416 | 1/1972 | Shepherd ........................... 427/2 X |
| 3,789,029 | 1/1974 | Hodosh |
| 3,808,606 | 5/1974 | Tronzo ..................................... 3/1.9 |
| 3,882,858 | 5/1975 | Klemm ........................... 128/92 G |
| 3,906,550 | 9/1975 | Rostoker |
| 3,919,773 | 11/1975 | Freeman |
| 3,930,076 | 12/1975 | Kliment ........................... 427/2 X |
| 3,943,045 | 3/1976 | Cordrey et al. ................... 3/1.9 X |
| 3,943,267 | 3/1976 | Randol ........................... 427/2 |
| 3,971,134 | 8/1976 | Bokros |
| 3,992,725 | 11/1976 | Homsy |
| 4,051,598 | 10/1977 | Sneer |
| 4,093,576 | 6/1978 | deWijn ........................... 128/92 G X |
| 4,118,532 | 8/1978 | Homsy |
| 4,131,597 | 12/1978 | Bluethgen et al. ............ 128/92 C X |
| 4,164,794 | 8/1979 | Spectar et al. |
| 4,178,686 | 12/1979 | Riess et al. ........................... 3/1.9 X |
| 4,181,983 | 1/1980 | Kulkarni ........................... 3/1.9 X |
| 4,186,448 | 9/1979 | Brekke |
| 4,199,864 | 5/1980 | Ashman |
| 4,244,689 | 1/1981 | Ashman ........................... 433/201 X |
| 4,247,287 | 3/1981 | Gigante |
| 4,252,525 | 3/1981 | Child |
| 4,266,303 | 5/1981 | Park ........................... 128/92 C X |

FOREIGN PATENT DOCUMENTS

| | | |
|---|---|---|
| 2255916 | 3/1973 | Fed. Rep. of Germany |
| 2449831 | 4/1975 | Fed. Rep. of Germany .......... 427/2 |
| 2105998 | 3/1972 | France |

OTHER PUBLICATIONS

Sterling Drug Inc., "Conagraf" Package Insert, Feb. 24, 1982.
P. Boyne and D. Cooksel, J. Am. Dent. Assn., 71, 1426-1435, (1965).
Hydron Laboratories Inc., Bibliography-Medical and Dental Applications of Hydron.
K. Kliment et al., J. Biomed. Mater. Res., 2, 237-243, (1968).
NPD Dental Systems, Inc., Abstract of Technical References-Hydron Root Canal Filling Material.
B. S. Levowitz et al., Trans. Amer. Soc. Artif. Int. Organs., vol. XIV, 82-88, (1968).
A. Ashman and P. Bruins, Oral Implantology, vol. X, (1982).
G. D. Winter and B. J. Simpson, Nature, 223, 88-90, (Jul. 5, 1969).
G. D. Winkler, Proc. Roy. Soc. Med., 63, 1111-1115, (Nov. 1970).
J. S. Calnan, Proc. Roy. Soc. Med., 63, 1115-1118, (Nov. 1970).
G. R. Taylor et al., Journal of Surgical Research, 11, 401-409, (Aug. 1971).
J. S. Calnan et al., Brit. J. Plastic Surgery, 24, 113-124, (1971).
S. Lerman and G. Sapp, Canad. J. Ophthal., 6, 1-8, (1971).
L. Sprincl et al., J. Biomed. Mater. Res., 4, 447-458, (1971).
M. F. Refojo, J. Biomed. Mater. Res., 5, 113-119, (1971).
L. Sprincl et al., Calc. Tiss. Res., 13, 63-72, (1973).
A. F. Hegyeli, J. Biomed. Mater. Res., 7, 205-214, (1973).
S. D. Bruck, J. Biomed. Mater. Res., 7, 387-404, (1973).
P. S. Walker et al., Rhiology of Biological Systems, 260-277, (1973).
J. H. S. Simon and J. T. Kimura, Oral Surgery, 37, 936-945, (Jun. 1974).
P. Nathan et al., Applied Microbiology, 28, 465-468, Sep. 1974).
M. Dumas and H. M. Myers, Int. J. Oral Surg., 3, 273-277, (1974).
C. D. Metz et al., J. Md. State Dental Assn., 17, 107-115, (1974).
R. H. Davis et al., Proceedings of the Society for Experimental Biology and Medicine, 147, 407-411, (1974).
J. A. Vale et al., British Medical Journal, 1, 5-9, (1975).
D. W. Rising et al., Journal of Endodontics, 1, (May 1975).
P. Nathan et al., Infection and Immunity, 12, 257-260, (Aug. 1975).
J. G. N. Swart et al., Polymer Preprints, 16, 368-371, (Aug. 1975).

(List continued on next page.)

Primary Examiner—Richard J. Apley
Assistant Examiner—David J. Isabella
Attorney, Agent, or Firm—Pennie & Edmonds

[57] ABSTRACT

This invention relates to implantable porous prostheses for use as bone or hard tissue replacements anywhere in the body. The porous implants comprise loose, individual polymeric particles of a specified size, coated with a hydrophilic material and barium sulfate particles. The prostheses are biologically compatible in the body and promote bone and tissue ingrowth and attachment. This invention also relates to a method for producing the novel prosthetic devices disclosed herein.

30 Claims, No Drawings

OTHER PUBLICATIONS

R. A. Abrahams and S. H. Ronel, *American Chemical Society Polymer Preprints*, 16, 535–540, (1975).

R. M. Rubin and J. L. Marshall, *J. Biomed. Mater. Res.*, 9, 375–380, (1975).

Z. Voldrich et al., *J. Biomed. Mater. Res.*, 9, 675–685, (1975).

D. G. Murray and J. S. Dow, *J. Biomed. Mater. Res.*, 9, 699–707, (1975).

B. M. Libin et al., *Journal of Periodontology*, 46, 51–56, (1975).

*Journal of the American Medical Association*, 236, 335–336, (Jul. 26, 1976).

B. H. Benkel et al., *Journal of Endodontics*, 2, 196–202, (Jul. 1976).

J. T. Mellonig et al., *Journal of Periodontology*, 46, 125–131, (1976).

P. Nathan et al., *Trans. Amer. Soc. Artif. Int. Organs*, vol. XXII, (1976).

P. Nathan et al., *American Burn Association, Ninth Annual Meeting*, (Mar. 31–Apr. 2, 1977).

J. J. Klawitter et al., *J. Dent. Res.*, 56, 385–393, (Apr. 1977).

J. Henahan, *Medical Tribune*, (May 11, 1977).

A. Ashman and M. L. Moss, *J. Prosthet. Dent.*, 37, 657–665, (Jun. 1977).

J. H. Kronman et al., *J. Dent. Res.*, 56, 795–801, (Jul. 1977).

B. V. Rejda et al., *ESAO II*, 62–67, (1977).

K. Robinson et al., *IADR Abstracts*, 379, (1978).

R. Green et al., *IADR Abstracts*, 380, (1978).

L. J. Peterson et al., *J. Dent. Res.*, 58, 489–496, (Jan. 1979).

L. B. Goldman et al., *Quintessence International* 2/1979, 101–107, (Feb. 1979).

J. H. Kronman et al., *Oral Surgery, Oral Medicine, Oral Pathology*, 48, 175–177, (Aug. 1979).

H. W. Denissen and K. de Groot, *The Journal of Prosthetic Dentistry*, 42, 551–556, (Nov. 1979).

H. G. Willert et al., *Arch. Orthop. Traumat. Surg.*, 94, 265–292, (1979).

A. Harrison et al., *J. Biomed. Mat. Res.*, 13, 23–34, (1979).

L. L. Hench, *Science*, 208, 826–831, (May 23, 1980).

H. W. Denissen et al., *Clinical Preventive Dentistry*, 2, 23–28, (Jul.–Aug. 1980).

POLYMERIC ACRYLIC PROTHESIS

TECHNICAL FIELD

This invention relates to prostheses for use as bone or hard tissue replacements in any part of the body. More particularly, it discloses porous implants which are biologically compatible in the body and promote bone and tissue ingrowth and attachment. This invention also relates to a method for producing the novel prosthetic devices disclosed herein.

BACKGROUND ART

In cases where an entire tooth/root, a section of bone or any hard tissue structure or defect must be replaced or repaired, biological compatibility and adequate ingrowth and attachment of surrounding body tissue and bone must be assured.

U.S. patent application Ser. No. 214,572, filed Dec. 8, 1980, to Bruins et al. and assigned to Medical Biological Sciences, Inc., the assignee herein, approaches these problems of compatibility and tissue ingrowth by providing prosthetic devices comprising selected-sized polymethylmethacrylate (PMMA) beads modified with small amounts of barium sulfate and coated with and physically bonded together by means of a polymerized hydroxyethyl methacrylate (PHEMA) coating. The resulting bonds between the PHEMA coated PMMA particles provide a basic foundation for porous implants having exceptional strength. Adequate bone and tissue ingrowth is insured by the use of the hydrophilic PHEMA coating which is wetted by the body fluids.

SUMMARY OF THE INVENTION

The present invention provides a prosthesis comprising a conglomeration of modified PMMA beads which are not, initially, bonded together. Specifically, "modified" PMMA beads according to the invention are described as loose, individual PMMA beads coated with PHEMA and further modified with barium sulfate for x-ray identification.

The loose, individual modified PMMA beads may be inserted into areas of bone defects, such as cavities, or packed into any hard tissue part of the body in which repair, reconstruction or replacement is indicated. Areas where the loose, individual modified PMMA beads may be used include, for example, the third molar socket where no replacement molar is desired; furcations or bony recessions between adjacent teeth roots and infra-bony pockets caused by gum and bone disease. Non-oral applications include: fracture healing, bone cancer replacement, bony buildup in plastic surgery, filling of defective bone areas and replacement of metal implants, as well as replacement of any failing metal implants.

DETAILED DESCRIPTION OF THE INVENTION

The prosthesis of this invention comprises a conglomeration of modified PMMA beads which, in individual, loose form, may, initially, be packed into cavities or other areas of hard tissue defect or disease by means of a dental tool such as, for example, the type used to transfer silver amalgam. When a void in a hard tissue area is completely filled with the loose, individual modified PMMA beads, the surrounding soft tissue is then sutured over the beads to completely enclose them. Once enclosed, the beads come into contact with each other, forming pores that are readily wettable by blood and body fluids. In this way, bone growth is promoted and bone recession prevented. As the healing process progresses, ingrowth of surrounding bone and/or tissue throughout the interstices of the packed beads leads to the formation of a prosthesis comprising a conglomeration of the modified PMMA beads.

Loose, non-bonded PMMA beads coated with PHEMA and modified with small particles of barium sulfate are produced in a process similar to that disclosed in the applicants' patent application Ser. No. 214,572, filed Dec. 8, 1980, which is herewith incorporated by reference. In order to prevent bonding of the PMMA beads, the relative barium sulfate content of the implants is increased, while the amount of PHEMA is decreased and pressure avoided. Any clumps formed by the coated PMMA particles are broken up by physical means, such as a mortar and pestle.

The loose, non-bonded modified PMMA beads comprising the hard tissue implants of this invention are produced according to the following method. PMMA beads are thoroughly mixed with between about 10 to 20% by volume, preferably 10%, and between about 21.5 and 43% by weight of 0.7 micron—or less than 1 micron—particle-size barium sulfate. Preferably, the size of the PMMA beads is chosen with a view towards the development of pore sizes that promote bone growth. Under various embodiments of the invention, the PMMA beads may be about the 20 to 24 mesh size (particle diameters between about 700 and 840 microns) or about the 24 to 30 mesh size (particle diameters between about 590 and 700 microns) which are most easily transferred and packed into a void in hard tissue areas, and which form a pore size which promotes bone growth. The PMMA may contain small amounts of a plasticizer or a comonomer.

Between about four and seven percent, preferably five percent by weight (based on the PMMA) of monomeric hydroxyethyl methacrylate (HEMA) is then added to the PMMA bead-barium sulfate mixture and the total mixture is then thoroughly mixed and combined to effect a uniform coating of the PMMA beads. The HEMA has a high grade of purity—about 98.4% minimum and is lightly inhibited from polymerizing by trace amounts of an inhibitor such as the methyl ether of hydroquinone (MEHQ). The HEMA is preferably modified by the addition of a cross-linking agent such as triethyleneglycol dimethacrylate, which comprises between about 1 and 5% of the HEMA, preferably 5%.

The mixed PMMA beads are subsequently heated while in a thin layer of about 1/16" to ⅛" in thickness in a silicone rubber mold or on a non-polar surface such as Teflon, polyethylene or polypropylene, that does not heat up in the alternating field and whose surface acts as a release agent. The heat treatment is carried out in a dielectric oven such as a Model MBS-1, manufactured by W. T. Rose and Associates of Troy, New York, until most of the hydroxyethyl methacrylate is polymerized. The heating step is, for example, about 1½ minutes in duration when the upper electrode is in a position ¼" above the top of the beads. The PMMA beads are then allowed to cool to an ambient temperature between about 70° to 80° F. and any clumps are broken up using a mortar and pestle and subsequently by screening.

Since the resulting modified PMMA beads may contain residual amounts of monomeric HEMA, the beads are then boiled in water for about 2 to 3 minutes in order to extract any remaining monomer. The PMMA beads are then spread out and air dried, or force dried under temperatures that are not high enough to cause melting.

The loose, non-bonded modified PMMA beads have a water-wettable PHEMA coating into which the barium sulfate particles are imbedded. All of the barium sulfate is attached to the PMMA beads and thus there are no free particles of barium sulfate remaining. The barium sulfate must be present in an amount to substantially prevent bonding between the PMMA particles. Therefore, if the amount of PHEMA coating is increased, a corresponding increase in the amount of barium sulfate used is required.

When the PMMA beads are to be packed into voids in hard tissue areas, it is advantageous that the PHEMA coating is wetted and swollen by water so that the beads become slightly adherent and can be more readily handled in clumps by a means of a dental tool, such as, for example, the type used to transfer silver amalgam.

Bone surfaces which will be adjacent to the prosthesis are advantageously pretreated in various ways. Preferably, any tartar or debris on the bone surface, as well as all diseased bone adjacent to the prosthesis should be removed. This may be accomplished by using, for example, a round dental burr. In oral applications, it is also desirable to remove any diseased bone, as well as all the tartar and debris on the tooth roots adjacent to the bone defect, by scaling and curettaging the root surfaces with either a periodontal instrument or an ultrasonic scaler. The cleaned root surface is then treated with a mild acid solution such as, for example, a 50% aqueous solution of citric acid or phosphoric acid, for about two minutes, followed by rinsing with water. The mild acid treatment serves to collagenize the root and thus promote reattachment.

It is understood that the foregoing detailed description is provided merely by way of illustration and that several modifications may be made therein without departing from the disclosed invention.

We claim:

1. A packing material for forming in vivo prosthetic implants for hard tissue, the packing material comprising disjoint micron sized particles, each particle having an inner core comprised of a first biologically-compatible polymeric material and having an outer coating generally surrounding the inner core, the outer coating being comprised of a second biologically-compatible polymeric material, the second polymeric material being hydrophilic and having a composition different from the composition of the first polymeric material, each particle incorporating a sufficient quantity of barium sulfate to render a prosthetic implant formed of a compacted mass of the particles visible in an X-ray radiograph, the particles being of a size to permit a mass of the disjoint particles to be packed in a body cavity having at least one surface comprised of a hard tissue to form a prosthetic implant for the hard tissue with interstices between compacted particles of the prosthetic implant forming pores into which tissue can grow.

2. The packing material of claim 1 in which the diameter of the particles is in the range of from about 590 microns to about 840 microns.

3. The packing material of claim 2 in which the cores of the particles are composed of an acrylic polymeric material.

4. The packing material of claim 3 in which the cores of the particles are polymethylmethacrylate beads.

5. The packing material of claim 4 in which the polymethylmethacrylate beads include a plasticizer.

6. The packing material of claim 3 in which the cores of the particles are composed of a copolymer of methylmethacrylate and a comonomer.

7. The packing material of claim 3 in which the hydrophilic polymeric material is a polymeric hydroxyethylmethacrylate.

8. A packing material for forming in vivo prosthetic implants for hard tissue, the packaging material comprising disjoint particles, having a diameter in the range of from about 590 microns to about 840 microns, each particle having an inner core comprised of a biologically-compatible acrylic polymeric material and having an outer coating generally surrounding the inner core, the outer coating being comprised of a biologically-compatible hydrophilic polymeric hydroxyethylmethacrylate material, the ratio of the weight of the polymeric hydroxyethylmethacrylate to the weight of the cores of the particles is in the range of from about 0.04 to about 0.07, each particle incorporating a sufficient quantity of barium sulfate to render a prosthetic implant formed of a compacted mass of the particles visible in an X-ray radiograph, the particles being of a size to permit a mass of the disjoint particles to be packed in a body cavity having a least one surface comprised of a hard tissue to form a prosthetic implant for the hard tissue with interstices between compacted particles of the prosthetic implant forming pores into which tissue can grow.

9. The packing material of claim 8 in which the polymeric hydroxyethylmethacrylate comprises a copolymer of monomeric hydroxyethylmethacrylate and a cross-linking agent.

10. The packing material of claim 9 in which the cross-linking agent is triethyleneglycol dimethacrylate.

11. The packing material of claim 10 in which the ratio of the weight of the triethyleneglycol dimethacrylate to the weight of the monomeric hydroxyethylmethacrylate is in the range of from about 0.01 to about 0.05.

12. The packing material of claim 8 in which the barium sulfate is located in the coating of hydrophilic polymeric material.

13. The packing material of claim 12 in which the ratio of the weight of the barium sulfate to the weight of the cores of the particles is in the range of from about 0.25 to about 0.43.

14. The packing material of claim 13 in which the barium sulfate is in the form of particles having a diameter of less than about one micron.

15. A packing material for forming in vivo prosthetic implants for hard tissue, the packing material comprising disjoint micron sized particles, each particle having an inner core comprised of a first biologically-compatible polymeric material and having an outer coating generally surrounding the inner core, the outer coating being comprised of a second biologically-compatible polymeric material, the second polymeric material being hydrophilic and having a composition different from the composition of the first polymeric material, each particle incorporating a radio-opaque material, the particles being of a size to permit a mass of the disjoint particles to be packed in a body cavity having at least one surface comprised of a hard tissue to form a prosthetic implant for the hard tissue with interstices between compacted particles of the prosthetic implant forming pores into which tissue can grow.

16. The packing material of claim 15 in which the diameter of the particles is in the range of from about 590 microns to about 840 microns.

17. The packing material of claim 16 in which the cores of the particles are composed of an acrylic polymeric material.

18. The packing material of claim 17 in which the cores of the particles are polymethylmethacrylate beads.

19. The packing material of claim 18 in which the polymethylmethacrylate beads include a plasticizer.

20. The packing material of claim 17 in which the cores of the particles are composed of a copolymer of methylmethacrylate and a comonomer.

21. The packing material of claim 17 in which the hydrophilic polymeric material is a polymeric hydroxyethylmethacrylate.

22. The packing material of claim 21 in which the ratio of the weight of the polymeric hydroxyethylmethacrylate to the weight of the cores of the particles is in the range of from about 0.04 to about 0.07.

23. The packing material of claim 22 in which the polymeric hydroxyethylmethacrylate comprises a copolymer of monomeric hydroxyethylmethacrylate and a cross-linking agent.

24. The packing material of claim 23 in which the cross-linking agent is triethyleneglycol dimethacrylate.

25. The packing material of claim 24 in which the ratio of the weight of the triethyleneglycol dimethacrylate to the weight of the monomeric hydroxyethylmethacrylate is in the range of from about 0.01 to about 0.05.

26. The packing material of claim 21 in which the radio-opaque material is barium sulfate.

27. The packing material of claim 26 in which the barium sulfate is located in the coating of hydrophilic polymeric material.

28. The packing material of claim 27 in which the ratio of the weight of the barium sulfate to the weight of the cores of the particles is in the range of from about 0.25 to about 0.43.

29. The packing material of claim 28 in which the barium sulfate is in the form of particles having a diameter of less than about one micron.

30. A packing material for forming in vivo prosthetic implants for hard tissue, the packing material comprising disjoint micron sized particles, each particle having an inner core comprised of a first biologically-compatible polymeric material and having an outer coating generally surrounding the inner core, the outer coating being comprised of a second biologically-compatible polymeric material, the second polymeric material being hydrophilic and having a composition different from the composition of the first polymeric material, each particle incorporating a sufficient quantity of barium sulfate to prevent bonding between the particles, the particles being of a size to permit a mass of the disjoint particles to be packed in a body cavity having at least one surface comprised of a hard tissue to form a prosthetic implant for the hard tissue with interstices between compacted particles of the prosthetic implant forming pores into which tissue can grow.

* * * * *